United States Patent [19]
Casperson et al.

[11] Patent Number: 6,004,805
[45] Date of Patent: *Dec. 21, 1999

[54] TRANSCRIPTIONAL ENHANCER FROM MILK PROTEIN GENES

[75] Inventors: Gerald F. Casperson, Ballwin, Mo.; Christian T. Schmidhauser; Mina J. Bissell, both of Berkeley, Calif.

[73] Assignee: G.D Searle & Co., Chicago, Ill.

[ * ] Notice: This patent is subject to a terminal disclaimer.

[21] Appl. No.: 07/891,541

[22] Filed: May 29, 1992

[51] Int. Cl.$^6$ ............................. C12N 5/10; C12N 1/00; C12N 15/11; C12N 15/79
[52] U.S. Cl. ...................... 435/325; 435/243; 435/320.1; 435/410; 536/24.1
[58] Field of Search .................................. 935/6, 27, 36, 935/41; 435/320.1, 243, 69.1, 455, 410; 536/24.1

[56] References Cited

U.S. PATENT DOCUMENTS 4,740,461  4/1988  Kaufman ................................ 435/69.1

OTHER PUBLICATIONS

Ponta, H. et al. (1985) Proceeding of the National Academy of Sciences, vol. 82, pp. 1020–1024.

Andres, A.–C., C.–A. Schönenberger, B. Groner, L. Henninghausen, M. LeMeur and P. Gerlinger (1987) *Proc. Natl. Acad. Sci. USA* 84, 1299–1303.

Andres, A.–C., M.A. van der Valk, C.–A. Schönenberger, F. Flückiger, M. LeMeur, P. Gerlinger and B. Groner (1988) *Genes Dev.* 2, 1486–1495.

Archibald, A.L., M. McClenaghan, V. Hornsey, J.P. Simons and A.J. Clark (1990) *Proc. Natl. Acad. Sci., USA* 87, 5178–5182.

Bühler, T.A., T. Buyère, D.F. Went, G. Stranzinger and K. Bürki (1990) *Biotechnol.* 8, 140–143.

Clark, A.J., H. Bessos, J.O. Bishop, P. Brown, S. Harris, R. Lathe, M. McClenaghan, C. Prowse, J.P. Simons, C.B.A. Whitelaw and I. Wilmut (1989) *Biotechnol.* 7, 487–492.

Dale, T.C., M.J. Krnacik, C. Schmidhauser, C.L.–Q. Yang, M.J. Bissell and J.M. Rosen (1992) *Molec. Cell. Biol.* 12, 905–914.

Dopplr, W., B. Groner and R.K. Ball (1989) *Proc. Natl. Acad. Sci., USA* 86, 104–108.

Doppler, W., W. Höck, P. Hofer, B. Groner (1990) *Endocrinol.* 4, 912–919.

Doppler, W., A. Villunger, P. Jennewein, K. Brduscha, B. Groner and R.K. Ball (1991) *Molec. Endocrinol.* 5, 1624–1632.

Ebert, K.M., J.P. Selgrath, P. DiTullo, J. Denman, T.E. Smith, M.A. Memon, J.E. Schindler, G.M. Monastersky, J.A. Vitale and K. Gordon (1991) *Biotechnol.* 9, 835–838.

Gordon, K., E. Lee, J.A. Vitale, A.E. Smith, H. Westphal and L. Hennighausen (1987) *Biotechnol.* 5, 1183–1187.

Greenberg, N.M., J.W. Anderson A.J.W. Hsueh, K. Nishimori, J.J. Reeves, D.M. deAvila, D.N. Ward and J.M. Rosen (1991) *Proc. Natl. Acad. Sci., USA* 88, 8327–8331.

Greenberg, N.M., T.V. Reding, T.Duffy, and J.M. Rosen (1991) *Molec. Endocrinol.* 5, 1504–1512.

Lee, C.S. and T. Oka (1992) *J. Biol. Chem.* 267, 5797–5801.

Lee, K.–F., S.H. Atiee, S.J. Henning and J.M. Rosen (1989a) *Mol. Endocrinol.* 3, 447–453.

Lee, K.–F., S.H. Atiee and J.M. Rosen (1989b) *Mol. Cell. Biol.* 9, 560–565.

Lesueur, L., M. Edery, J. Paly, J. Clark. P.A. Kelly and J. Djiane (1990) *Molec. Cell. Endocrinol.* 71, R7–R12.

Meade, H., L. Gates, E. Lacy and N. Lonberg (1990) *Biotechnol.* 8, 443–446.

Pittius, C. W., L. Hennighausen, E. Lee, H. Westphal, E. Nichols, J. Vitale and K. Gordon (1988) *Proc. Natl. Acad. Sci., USA* 85, 5874–5878.

Schmidhauser, C., M.J. Bissell, C.A. Myers, and G.F. Casperson (1990) *Proc. Natl. Acad. Sci. USA* 87, 9118–9122.

Schmidhauser, C., G.F. Casperson, C.A. Myers, K.T. Sanzo, S. Bolten, M.J. Bissell (1992) *Molec. Biol. Cell 3*, 699–709.

Schmitt–Ney, M., W. Doppler, R.K. Ball and B. Groner (1991) *Molec. Cell. Biol.* 11, 3745–3755.

Schmitt–Ney, M., B. Happ, R.K. Ball and B. Groner (1992) *Proc. Natl. Acad. Sci., USA* 89, 3130–3134.

Schoenenberger, C.–A., A.–C. Andres, B. Groner, M. van der Valk, M. LeMeur and P. Gerlinger (1988) *EMBO J.* 7, 169–175.

Simons, J.P., I. Wilmut, A.J. Clark, A.L. Archibald, J.O. Bishop and R. Lathe (1988) *Biotechnol.* 6, 179–183.

Soulier, S., J.L. Vilotte, M.G. Stinnakre and J.C. Mercier (1992) *FEBS Lett* 297,13–18.

Stinnakre, M.G., J.L. Vilotte, S. Soulier, R. L Haridon, M. Charlier, P. Gaye, and J.C. Mercier (1991) *FEBS Lett.* 284, 19–22.

Wright, G., A. Carver, D. Cottom, D. Reeves, A. Scott, P. Simons, I. Wilmut, I. Garner and A. Colman (1991) *Biotechnol.* 9, 830–834.

Yoshimura, M. and T. Oka (1990) *Proc. Natl. Acad. Sci., USA* 87, 3670–3674.

*Primary Examiner*—Terry McKelvey
*Attorney, Agent, or Firm*—Dennis A. Bennett

[57] ABSTRACT

The invention relates to novel enhancer nucleotide sequences which stimulate transcription of heterologous DNA in cells in culture. The enhancers are derived from major milk protein genes by the process of deletion mapping and functional analysis. The invention also relates to expression vectors containing the novel enhancers.

10 Claims, 8 Drawing Sheets

```
  1 GACAGTCATT AGGAAATTCT CTGTTTATTG CACAATATGT AAAGCATCTT
 51 CCTGAGAAAA GGGAAATGTT GAATGGGAAG GACATGCTTT CTTTTGTATT
101 CCTTTTCTCA GAAATCACAC TTTTTTGCCT GTGGCCTTGG CAACCAAAAG
151 CTAACACATA
```

Fig. 4

1    TCTAGAGAAT AAGATTGACA TTCCCTGGAG TCACAGCATG CTTTGTCTGC
51   CATTATCTGA CCCCTTTCTC TTTCTCTCTT CTCACCTCCA TCTACTCCTT
101  TTTCCTTGCA ATACAT

SEQUENCE LISTING (1) GENERAL INFORMATION:

(iii) NUMBER OF SEQUENCES: 2

(2) INFORMATION FOR SEQ ID NO:1:

```
        (i) SEQUENCE CHARACTERISTICS:
            (A) LENGTH: 160 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:1:

GACAGTCATT AGGAAATTCT CTGTTTATTG CACAATATGT AAAGCATCTT CCTGAGAAAA      60

GGGAAATGTT GAATGGGAAG GACATGCTTT CTTTTGTATT CCTTTTCTCA GAAATCACAC     120

TTTTTTGCCT GTGGCCTTGG CAACCAAAAG CTAACACATA                          160

(2) INFORMATION FOR SEQ ID NO:2:

(i) SEQUENCE CHARACTERISTICS:
            (A) LENGTH: 116 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:2:

TCTAGAGAAT AAGATTGACA TTCCCTGGAG TCACAGCATG CTTTGTCTGC CATTATCTGA      60

CCCCTTTCTC TTTCTCTCTT CTCACCTCCA TCTACTCCTT TTTCCTTGCA ATACAT        116
```

TRANSCRIPTIONAL ENHANCER FROM MILK PROTEIN GENES

The government owns rights in the present invention pursuant to grant number DE-AC03-76SF00098 from the Department of Energy.

FIELD OF THE INVENTION

The field of this invention relates to gene expression more particular to stimulating transcription of heterologous DNA in mammalian cells in culture.

BACKGROUND

Gene expression in eukaryotic cells is regulated by DNA sequences found primarily (although not exclusively) in the region upstream (5' ward) of the transcription start site. These DNA sequences fall into two broad categories promoters and enhancers.(Maniatis et al. 1987) Promoter sequences generally, but not exclusively fall within about 100 base pairs (bp) of the transcription start site. The promoter determines the direction of transcription and the position at which transcription begins. Promoter sequences may or may not be active, in and of themselves, in directing expression (transcription) of genes or DNA sequences found downstream. Enhancer elements on the other hand, are DNA sequences generally found more than 100 bp from the transcription start site. Enchancers increase the rate of initiation of transcription from promoter sequences. Enhancers stimulate transcription by serving as binding sites for nuclear proteins. These proteins increase the rate of initiation by interacting with the proteins of the transcription initiation complex assembled on the promoter. These enhancer binding proteins stimulate transcription by an as yet unknown mechanism. Some of the properties of enhancers are known, however. These include:

1. Enhancers activate transcription from a distance. The distance may vary, depending on the particular enhancer, from less than 250 bp from the transcription start site to many thousands of bp (kbp) away (Serfling, et al., 1985; Banerji, et al., 1981; Grosschedl and Birnsteil, 1980).

2. Enhancer activity is independent of distance from the transcription start site. Individual enhancers may be moved, with respect to the transcription start site, without materially affecting their activity. Indeed, enhancers may be moved from the 5'-flanking DNA (Serfling, et al., 1981) (upstream of the transcription start site) to the 3'-flanking region (downstream of transcribed sequences) (Banerji, et al., 1981) or even within the transcription units (Gillieg, et al., 1983; Banerji, et al., 1983) and still function in stimulating transcription.

3. Enhancer activity is non-directional. Enhancer elements may be invered without affecting their activity (Grosschedl & Birnstiel, 1980; Banerji, et al., 1981). These properties distinguish enhancers from promoter elements (which may also stimulate transcription) in that promoter elements usually function only at a small distance from the transcription start site and only in a set orientation (Maniatis, et al., 1987). Such elements lose activity when moved or inverted. Transcription, having begun within the proximal promoter sequences, proceeds through the structural gene (the DNA sequences which encode a protein, also referred to as the transcription unit) and terminates within a DNA sequence (terminator) that specifies cessation of transcription and proper processing of the 3' terminus of the mRNA.

These various elements of a eukaryotic gene—enhancer, promoter, structural gene, and terminator—are modular and may be interchanged with DNA sequences of similar functions from other genes (Kaufman, 1990). If the structural gene encodes a protein whose production is desired either for sale or for research purposes, the assemblage is referred to as an expression cassette. The expression cassette's function is to direct transcription of whatever structural gene it contains, when introduced into a cell (whether grown in culture or contained within an animal). The particular cell must, of course, produce the nuclear proteins necessary to the functioning of the various parts of the expression cassette such as the enhancer-binding proteins.

Enhancers and their cognate nuclear proteins have been described from many sources. For example: the yeast (S. cerivisiae) GAL4 protein binds DNA sequences upstream of the GAL1 and GAL10 promoters and stimulates transcription (Johnston, 1987). The adenovirus E1A (Hearing & Schenk, 1986) and the Herpes simplex virus VP16 (Campbell, et al., 1984) proteins serve similar functions by binding DNA sequences within their respective viral genomes. VP16 acts as a transactivating protein in conjunction with a cellular transactivator called Oct 1, while the E1A protein acts alone. Similarly, proteins such as the glucocorticoid receptor, found in animal cells, stimulate transcription by binding their cognate enhancers within the genomes of animal cells.

The major milk protein genes of mammals are among the most highly expressed genes in any eukaryotic cell. For example, α-casein and β-casein mRNA's together account for nearly half of all the mRNA in lactating mammary epithelial cells (Mercier, et al., 1985).

The enhancer and promoter elements responsible for this high level of expression will be useful in designing eukaryotic cell expression vectors based on strong cellular enhancers and promoters. Current expression vectors, utilizing enhancers and promoters from viral or cellular genes (Kaufman, 1990; Kriegler, 1990), produce less mRNA than major milk protein promoters (Mercier, et al., 1985).

The search for the expression control elements (enhancers and promoters) of major milk protein genes began about 10 years ago with the isolation of cDNAs (Richards, et al., 1981; Willis, et al., 1982) and genes (Yu-Lee, et al., 1983; Campbell, et al., 1984; Jones, et al., 1985) encoding rat β- and α-casein and whey acidic protein (WAP). The genes for many major milk proteins of various species have now been cloned (reviewed in Mercier, et al., 1991) including the bovine β-casein gene (Gorodetsky, et al., 1990; Schmidhauser, et al., 1990). Comparison of the primary nucleotide sequences found immediately upstream of the mRNA start site showed extensive sequence homology among the related alpha and beta casein genes, between −150 (150 bp upstream of the mRNA start site) and +40 (Yu-Lee, et al., 1986). In particular, the region between −150 and −100 (termed the "milk box"; Rosen, 1987) was also identified in the α-lactalbumin and WAP promoters.

Functional analysis of the expression control elements of the major milk protein genes began with the introduction of intact genes from other species into the genomes of transgenic mice. These included the rat β-casein gene (Lee, et al., 1988), the rat and mouse whey acidic protein (AWP) genes (Bayna & Rosen, 1990; Burdon, et al., 1991), the sheep β-lactoglobulin gene (Simons, et al., 1987), and the bovine and guinea pig α-lactalbumin genes (Maschio, et al., 1991; Vilotte, et al., 1989). The transgenes included the structural genes (introns and exons) for each protein and varying amounts of 3'- and 5'-flanking DNA. Each xenogeneic transgene was expressed predominantly in the mammary gland of female animals during lactation. These results indicated that each gene contained the expression control elements necessary for tissue-specific, developmentally-appropriate regulation of expression.

Various groups have reported expression of heterologous proteins in the mammary glands of transgenic animals using expression control elements from major milk protein genes. These include the oncogenes Ha-ras (Andres, et al., 1987) and c-myc (Schnenberger et al., 1988), human tissue plasminogen activator (Pittius, et al., 1988; Gordon, et al., 1987; Ebert, et al., 1991) the *E.coli* CAT gene (Lee, et al., 1989 a,b), human interleukin-2 (Bühler, et al., 1990), clotting factor IX (Clark et al., 1989; Simons et al., 1988), and human alpha-1-antitrypsin (Wright, et al., 1991; Meade et al., 1990).

Collectively, these studies showed that the control elements necessary for appropriate temporal and tissue specific regulation generally reside in the 5' flanking regions of most major milk protein genes while some elements responsible for high level expression may reside elsewhere in some genes. Because of the relative difficulty and expense of generating transgenic mice, it has not been possible to map individual expression control elements in this way.

Several major milk protein promoters have been studied in less complex systems that allow more complete analysis. Transfection of MMP promoter-reporter gene constructs into functional mammary epithelial cell lines such as HC11 (Ball, et al., 1988) and C1D9 (Schmidhauser et al., 1990) allows much more rapid and relatively less expensive and time consuming analysis of transcriptional activity. Such studies allow analysis of hormonal and substratum effects on gene expression. Elements of the mouse WAP gene necessary for prolactin and glucocorticoid induction have been localized (by functional analysis of promoter deletions in HC11 cells) to between −1500 and −450 while cell-type specific elements were localized to between −2500 and −1500 and between −450 and the transcript initiation site (Doppler et al., 1991).

Similar deletion analysis of the rat β-casein promoter (Doppler et al., 1989) localized control elements important for hormonal regulation (prolactin and glucocorticoid) to between −2300 and −330, between −285 and −265 and between −190 and −170. These elements were not tested by inversion or by moving them with respect to the transcription start site so that no conclusions could be drawn regarding the presence or absence of transcriptional enhancers in these regions. Yoshimura and Oka (1990) showed that deletion of the region between −5300 and −545 of the mouse β-casein gene had little effect on expression in transfected rabbit mammary epithelial cells.

The promoter regions of several major milk protein genes have been tested for nuclear protein binding by biochemical techniques such as electrophoretic mobility shift and DNaseI protection. The bovine β-casein promoter contains a site (between −264 and −239) that binds the purified transcription factor NF1 (Kabishev, et al., 1990; Ivanov et al., 1990). The functional significance of this potential NF1 binding site is not known. Nuclear extracts from mammary tissue contain several proteins that interact with the region between −354 and −88 of the rat WAP promoter (Lubon and Hennighausen, 1987). Similarly, the region from −125 to −85 of the rat α-lactalbumin promoter is protected from nuclease digestion by proteins in mammary nuclear extracts (Lubon and Hennighausen, 1988). Functional tests of the importance of these regions in expression of the WAP and α-lactalbumin genes have not yet been carried out.

Detection of nuclear protein binding to major milk protein promoters helps to locate DNA sequences important to regulation of gene expression. However, functional analysis of the role of putative binding sites in gene expression must be carried out before definite conclusions can be drawn. Such analyses have been carried out in two cases. Lee and Oka (1992) detected mammary-specific protein binding to two regions of the mouse β-casein promoter. Methylation interference experiments indicated that the guanosine residues at −8 and −350 were involved in the binding. Analysis of transcriptional activity of wild type promoters and of promoters with mutations in the binding regions indicated that these sites were involved in progesterone-mediated repression of transcription.

Schmitt-Ney, et al., (1991) identified binding sites for five nuclear proteins within the rat β-casein promoter. Four were found in HC11 cell nuclear extracts. Two of the HC11 activities increased (activities C & D) and two decreased (activities A & B) following hormonal induction of casein expression. The A & B activities are thought to mediate repression because mutations affecting A binding caused an increase in basal (uninduced) promoter activity. The fifth binding activity, termed MGF, was found only in pregnant and lactating mammary gland (but not in HC11 cells). MGF binds to two sites, one between −80 and −100 and the other between −130 and −150. These sequences are conserved in other casein genes and in casein genes of other species. Mutations in the MGF binding sites that decrease protein binding also decrease transcriptional activity (Schmitt-Ney, et al., 1991, 1992).

BRIEF SUMMARY OF THE INVENTION

Figure 4:
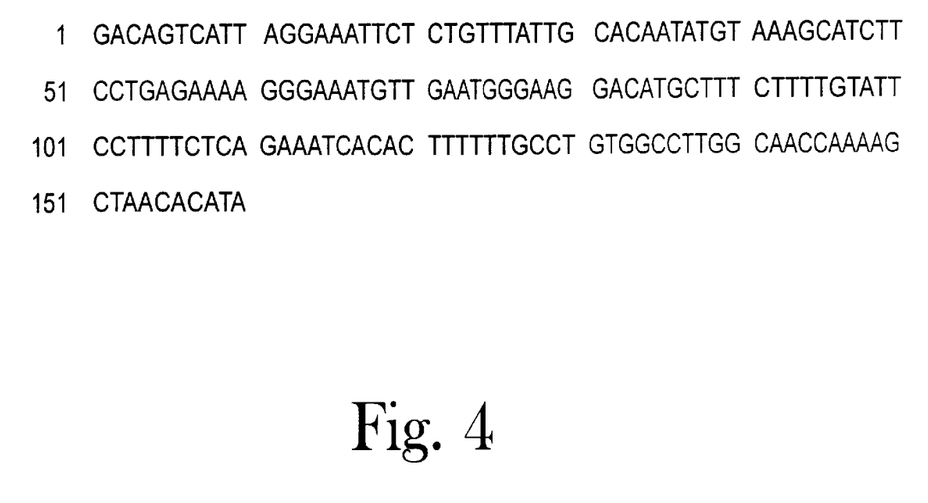
FIG. 4 Shows the nucleotide sequence of the enhancer BCE1. (SEQ. ID NO:1).
Figure 5:
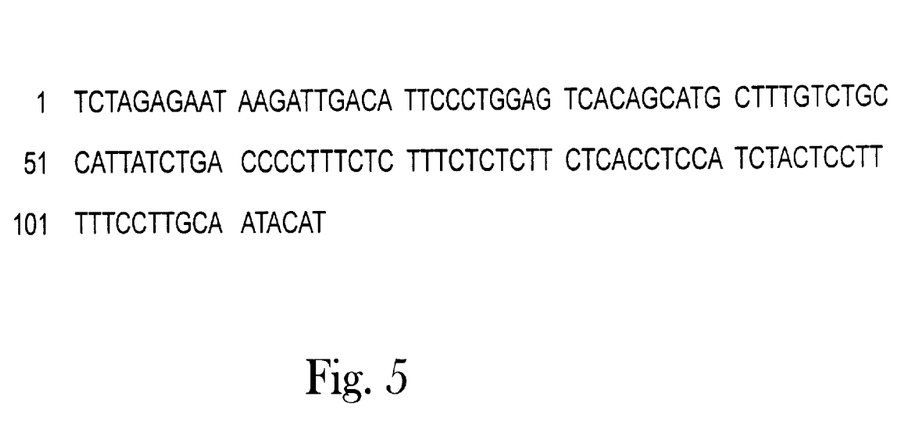
FIG. 5 Shows the nucleotide sequence of BCE2. (SEQ. ID NO:2).

In accordance with the present invention there is provided novel enhancers which have been derived from major milk protein genes which comprises the nucleotide sequences as shown in FIG. 4 and FIG. 5. and the nucleotide sequences are not more than 1 kilobase. Preferably the nucleotide sequences are not more than 500 bases and more preferably the nucleotide sequences consist of FIG. 4 and FIG. 5.

In another aspect of the invention there is provided an expression vector, comprising:

a) an enhancer derived from a major milk protein gene obtained by the process of deletion mapping and functional analysis;

b) a heterologous promoter operably linked to said enhancer which includes proximal transcriptional control elements and a transcription start site;

c) a DNA fragment encoding a protein linked downstream of said promoter (structural gene or cDNA); and d) a terminator linked downstream of said DNA fragment (from C) which includes a transcription termination signal and poly adenylation signal.

DETAILED DESCRIPTION

One aspect of this invention comprises a eukaryotic cell (whether grown in culture or contained within an animal), which is capable of high level expression of a heterologous structural gene or cDNA. The eukaryotic cell (preferably mammalian, with mammary epithelial cells being especially preferred) contains single or multiple copies of an expression cassette which is integrated into the cellular genome or maintained as an episome.

The expression vector comprising an enhancer element or elements derived from a mammalian major milk protein gene which may be in association with other enhancers not so derived. The enhancers serve to activate and/or stimulate transcription arising within promoter sequences found in productive association with the enhancers. The proximal promoter elements may be derived from viral genes or eukaryotic cellular genes whether of major milk protein origin or not. The expression cassette further consists of a heterologous structural gene and transcription termination sequence. Selection of the promoter and termination sequences are within the state of the art. Major milk proteins are those proteins found abundantly in milk. Most major milk proteins are produced only by mammary epithelial cells.

Heterologous structural genes include, among others, those encoding the following proteins; chloroampherical acetyl transferase (CAT), human tissue-type plasminogen activator (tPA), bovine somatotropin (BST), interleukin-3, cellular adhesion molecules such as ICAM1 and ELAM1 and variants of such molecules.

The major milk protein gene-derived enhancer, being derived from a gene which is very active transcriptionally, serves to increase promoter activity or efficiency and so to increase transcription of the heterologous structural gene. In order to so function, the host cell must produce the nuclear protein specific to the particular major milk protein-derived enhancer (and for other enhancers, if present). Expression of such nuclear proteins may arise naturally due to inherent properties of the chosen cell or by introduction into the cell of an expression cassette whose heterologous structural gene encodes the appropriate nuclear protein.

The 5' flanking regions of major milk protein genes can drive transcription of heterologous genes when introduced into mammalian cells in culture. The 5'-flanking regions contain novel enhancer elements which stimulate transcription when used in conjunction with proximal promoter elements derived from major milk protein genes and from heterologous promoters.

The bovine βcasein (bβcas) gene was isolated from a library of bovine genomic DNA fragments (Zurfluh et al., 1990) cloned in the phage vector EMBL4 (Schmidhauser, et al., 1990). Five clones were isolated that contained overlapping bovine genomic DNA inserts that together spanned 27 kilobases (Kb) of the bovine genome. The cloned DNA contained the bβcas gene. The cloned DNA contained the bβcas transcription unit on a 9 Kb Ecori fragment as well as 4 Kb of 5' flanking and 14 Kb of 3' flanking DNA (Schmidhauser, et al., 1990). The restriction map and nucleotide sequence of the 5'-flanking region (Schmidhauser, et al., 1990) agree well with those previously reported for the bβcas gene (Gorodetsky, et al., 1990).

In order to study the bβcas promoter and to discover novel enhancer elements therein, it was first necessary to develop a cell line that could be transfected with exogenous DNA and that could express major milk protein genes (Schmidhauser, et al., 1990).

A confluent culture of COMMA-1D cells (Danielson, et al., 1984) was treated with trypsin for different lengths of time. At each time point, detached cells were plated onto EHS and cultured for 3 days in medium containing all three lactogenic hormones. The cells cultured on EHS were then treated with trypsin again and dissociated to a single cell suspension. Cytospins of these cells were analyzed with a monoclonal antibody directed against β-casein. Cells with a greater resistance to trypsin treatment had a much higher frequency of β-casein expression. Passage 10 cultures of COMMA-1D contained 8% β-casein-producing cells. The first trypsin-treated subpopulation (those released first) had a reduced frequency of 4% β-casein production (probably due to fibroblast-like enrichment). Increasing the length of trypsin treatment released subpopulations progressively enriched in casein-producing cells; in the last fraction, 37% of cells stained for β-casein (Schmidhauser, et al., 1990). This subpopulation (designated C1D 9), enriched in casein-producing cells, formed spherical, aveolar structures on EHS with a similar morphology to primary mouse mammary cells. In addition, the level of casein mRNA was only slightly reduced in CID 9 cells compared to $t_0$ cells or primary cultures produced from 15-day pregnant mouse mammary gland. In CID 9 cells, β-casein expression was completely dependent on substrata. Little or no β-casein mRNA was detectable in cells grown on plastic for 6 days in the presence of all three lactogenic hormones (Schmidhauser, et al., 1990).

The profile of milk protein synthesis confirmed the substratum dependency of differentiation. Cells cultured in EHS, but not on plastic, expressed large amounts of caseins and transferrin. Furthermore, the pattern of milk protein secretion was analogous to primary culture (Bacellos-Huff, et al., 1989)—i.e., there was bidirectional secretion of transferrin and unidirectional secretion of β-casein into the lumen. Little or no β-casein could be detected when cells were cultured on plastic (Schmidhauser, et al., 1990).

In order to demonstrate that the bβcas gene could be transcribed in C1D9 cells, we transfected C1D9 cells as follows with a 16 Kb KpnI to BamHI fragment (K1.9B17.5) of the bβcas gene.

C1D9 cells were grown in DMEM/F12 (1:1) containing 5% heat-inactivated fetal calf serum (FCS), gentamicin (50 μg/ml), and insulin (5 μg/ml). Transfection was accomplished by calcium phosphate precipitation. Calcium phosphate precipitation was carried out according to the protocol of Gorman (1986), using 40 μg of DNA per 100-mm dish. G418 (GIBCO; 400 μ/ml) selection was started 48 hr after transfection. Surviving colonies were pooled and expanded for stocks and assays.

For hormonal and ECM-dependent milk protein induction, the cells were plated on plastic dishes or reconstituted basement membrane EHS (15) at $8 \times 10^4$ cells per cm² in the presence of 2% FCS and insulin. Hydrocortisone (Sigma; 1 μg/ml) and/or ovine prolactin (National Institutes of Health; 3 μg/ml) was added as indicated. Twenty-four hours after plating, the medium was switched to 0% FCS.

Total RNA was isolated as described (Chomczynski & Sacchi, 1987). Random-primed probe (Feinberg & Vogelstein, 1984) was prepared by using gel-purified insert sequences from a plasmid containing 540 base pairs (bp) of β-casein cDNA.

Cells transfected with pK1.9B17.5 were plated under various conditions and expression of the bβcas and the mouse β-casein (mβcas) genes were assayed by Northern analysis of extracted RNA. Expression of bβcas mRNA from transfected K1.9B16.5 DNA was three to four fold lower than for the endogenous mβcas gene. Regulation of the endogenous and transfected genes were, however, nearly identical. Expression of either gene was maximal in cells plated on EHS in the presence of IHP. Cells plated on plastic or cultured in the absence of prolactin produced far less β-casein mRNA. Cells cultured without hydrocortisone produced 2–4 fold less β-casein mRNA. Thus, the 16 kb K1.9B17.5 bβcas gene fragment contains not only the bβcas structural gene, but all promoter elements necessary for high-level expression and appropriate hormonal and ECM-dependent regulation of transcription (Schmidhauser, et al., 1990).

A series of bovine β-casein-CAT fusion genes were constructed with various lengths of 5' flanking bβcas DNA attached to the CAT gene at nucleotide +42 of the first, noncoding bovine β-casein exon. These plasmids were cotransfected with pSV2neo to confer antibiotic resistance. After G418 selection, between 100 and 500 colonies were pooled and cultured on different substrata in defined medium containing different hormone combinations.

For CAT assays, differentiated cells were harvested by digesting the EHS with dispase (Collaborative Research). CAT assays were carried out in a two-phase diffusion system (Neumann, et al., 1987) using [$^{14}$C]acetyl coenzyme A (NEN; 4 mCi/mmol, 1 Ci=37 GBq) at 0.1 μCi per assay. The reactions were carried out at room temperature. CAT activity was calculated as substrate conversion per min per μg of protein.

Cells transfected with bβcas–789+42/CAT contained maximal CAT activity of 0.7 (relative substrate conversion per min per μg of protein) when cultured on EHS ihp unless otherwise specified, CAT activities are from cells cultured under optimal hormonal (ihp) and substrate (EHS) conditions (Schidhauser et al, 1990). Using bβcas–1790+42/CAT, the CAT activity of the lysates was 9.4; a 17.7-fold increase. The CAT activity of the lysates was 37.5 with the bβcas–2605+42/CAT construct, a 3.7-fold increase compared with the bβcas–1790+42/CAT construct or a 48-fold increase compared with the bβcas–791+42/CAT construct. When cells were transfected with bβcas–3815+42/CAT, the activity dropped to 14.1 (Schmidhauser et al., 1990).

ECM stimulation of transcription from both bβcas–3815+42/CAT and the bβcas–2605+42/CAT was 38-fold reached 167-fold for the bβcas–1790+42/CAT construct. The bβcas–789+42/CAT still showed some ECM dependency (1.8-fold) but the induction was strongly reduced.

To examine whether transfected bovine β-casein-CAT fusion genes were hormonally regulated, we plated the stably transfected cells in defined medium containing different hormone combinations. Hydrocortisone-increased CAT expression 1.7-fold for the bβcas–3815+42/CAT construct, 7.4-fold induction for bβcas–2605+42/CAT 5.5-fold for the bβcas–1790+42/CAT construct, and an 8.1-fold induction for the shortest bβcas–791+42/CAT construct. When prolactin was omitted, no significant CAT expression was detected with any of the constructs.

We concluded from these studies (which have been published in Schmidhauser, et al., 1990) that the promoter elements necessary for high level expression from the bβcas promoter resided in the region between –1790 and +42 of the bβcas gene. We, therefore, carried out a more detailed analysis of this region.

Figure 1:
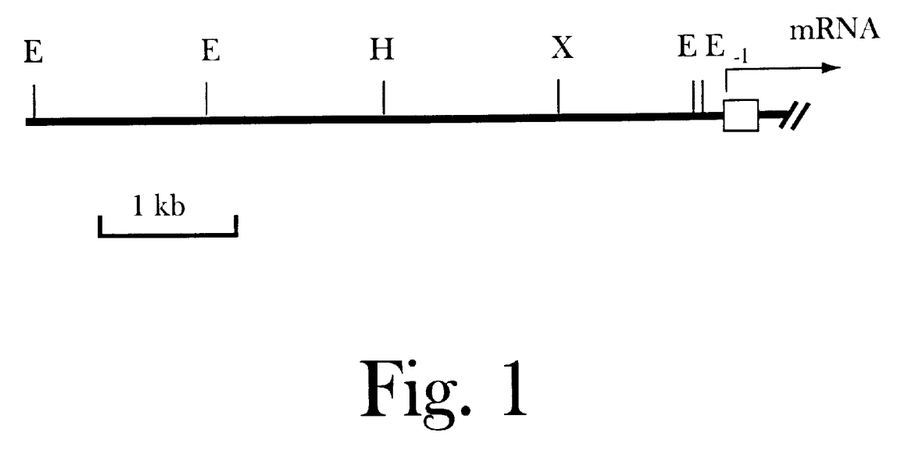
FIG. 1 Shows restriction map of the 5' flanking region of the bovine β-casein gene. E=EcoRI, H=HindIII, X=XbaI. The XbaI and HindIII sites are at −791 and −1790, respectively.
Figure 2:
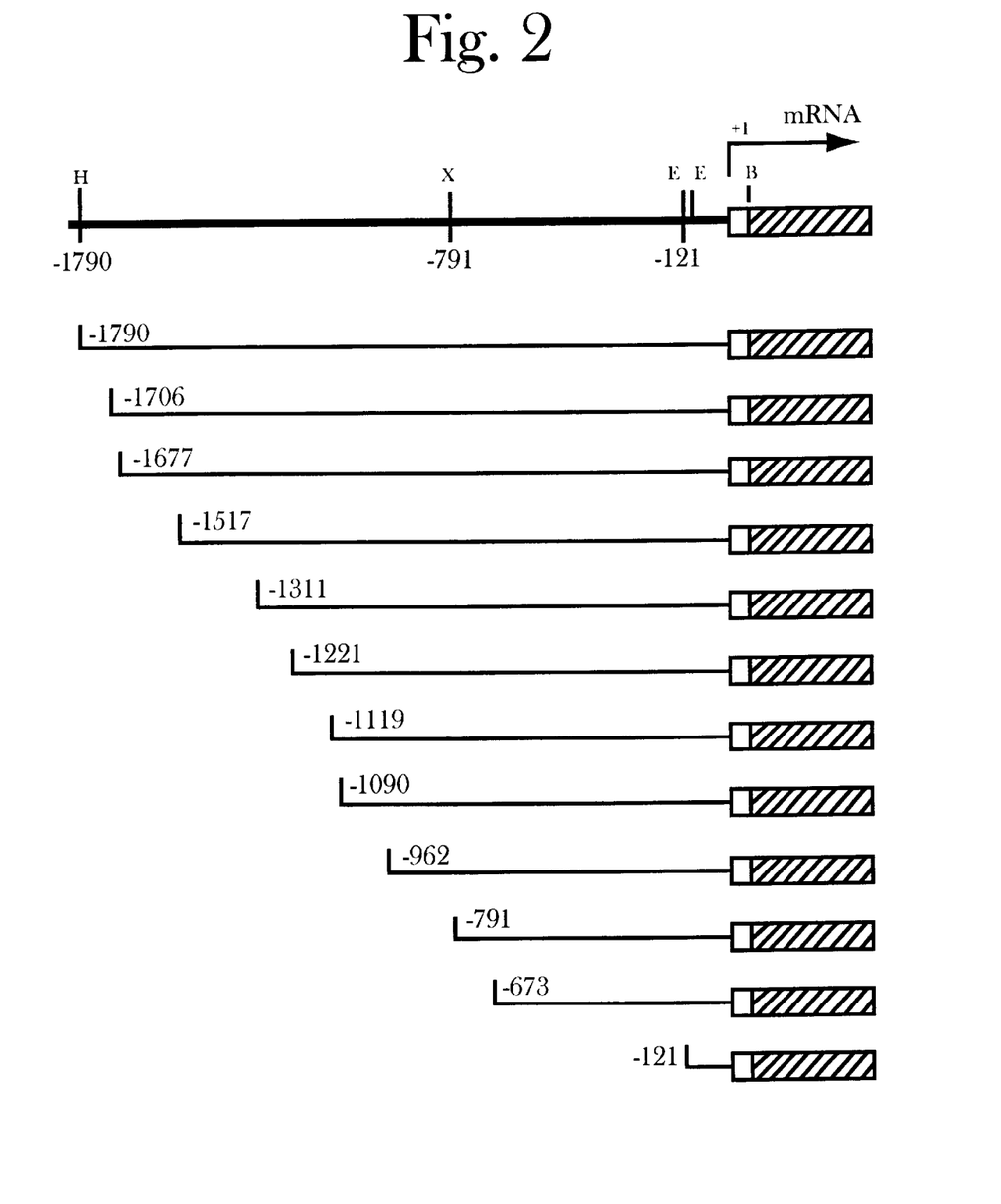
FIG. 2 Shows bovine β-casein 5'-flanking regions deletions fused to CAT. β-casein sequences are represented by the solid lines (5'-flanking regions) and open boxes (exons). CAT is represented by the hatched box.

Progressive deletions were made from the 5' ends of the bβcas promoters in bβcas–1790+42/CAT and bβcas–791+42/CAT using an Erase-a-Base kit (Pro Mega) according to the manufacturers instructions (a map of this region is shown in FIG. 1. The precise 5' ends of these deletions were determined by DNA sequencing (Sanger et al., 1977). A panel of bβcas promoters with 5' ends 100–200 bp apart and spanning to region between –1790 and –312 were selected (FIG. 2). The final deletion (ER1 FIG. 2) as constructed by deletion of bβcas sequences upstream of the EcoRI site at –121 in bβcas–791+42/CAT. These constructs were introduced into C1D9 cells as before and transcriptional activity was determined by measuring CAT accumulation in the stably-transfected cells. CAT assays were performed as above, or using thin layer chromatography according to Sambook, et al., (1989).

Figure 3:
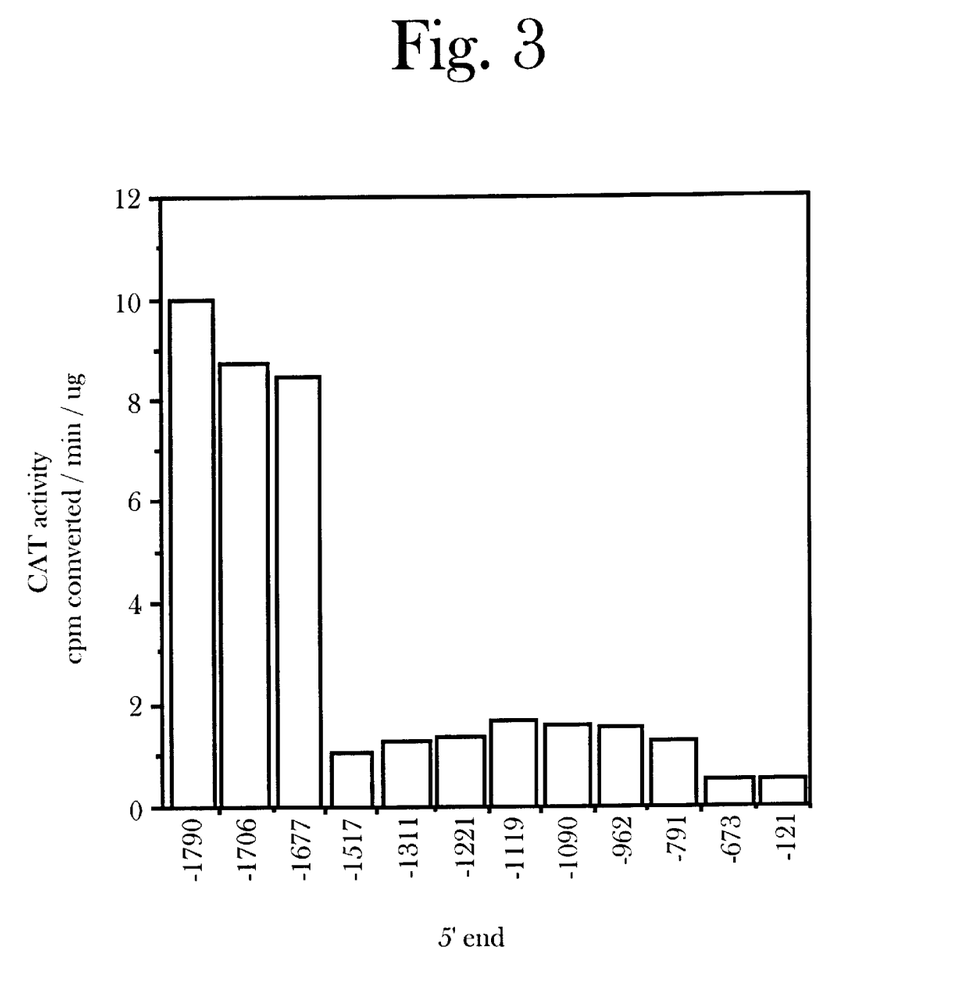
FIG. 3 Shows CAT activity expressed in C1D9 cells transfected with bovine β-casein promoter deletions fused to CAT.

Deletion of the region between –1676 and –1517 resulted in a 17-fold decrease in CAT expression (FIG. 3). We designated this region BCE1. No other deletions in the region between –1790 and –791 had any significant impact on CAT expression. Deletion of the region between –789 and –673 designated BCE2, resulted in an 8-fold decrease in CAT expression (FIG. 3). We concluded that BCE1 and BCE2 contain important elements for stimulation of β-casein gene expression. The two shortest promoter, bβcas –121+42 (designated ER-1), displayed no transcriptional activity under any conditions (FIG. 3). The nucleotide sequences of BCE1 and BCE2 are shown in FIGS. 4 and 5.

Figure 6:
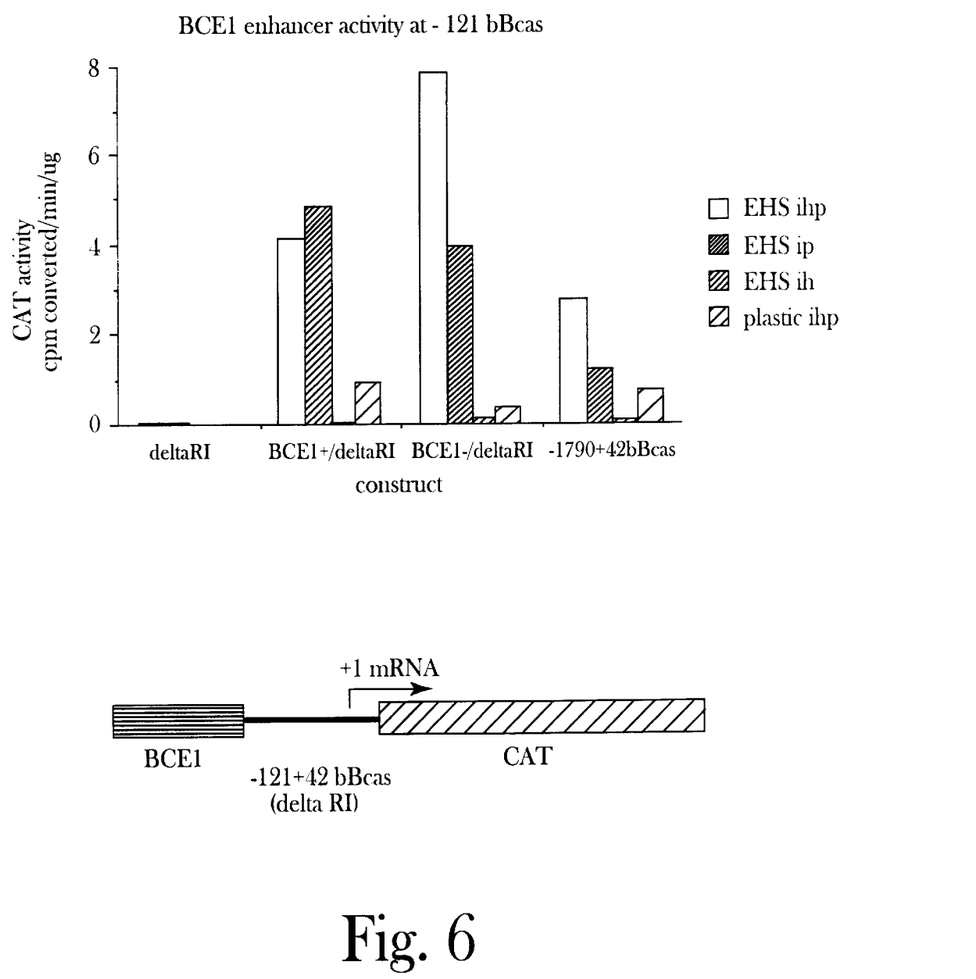
FIG. 6 Shows enhancer activity of BCE1 when fused as shown to the −121+42 bβcas promoter. C1D9 cells containing these constructs were plated under the conditions shownand CAT activity was determined.

We tested BCE1 in conjunction with the inactive bβcas promoter fragment ER-1. No CAT expression could be detected from the ER-1 promoter in C1D 9 cells (FIG. 6). However, BCE1 linked upstream of ER-1, reconstituted a promoter with considerable activity. Indeed, BCE1/ER-1/CAT expressed 1.5 to 2.5 fold more CAT activity than bβcas –1790+42/CAT which contains BCE1 in its normal context.

These studies showed that BCE1 restored transcriptional activity to the inactive ER-1 promoter. We therefore investigated the hormonal and ECM-dependent regulation of ER-1 fused to BCE1. CAT expression from both BCE1/ER-1 fusions was strongly dependent on the presence of ECM (FIG. 6, E ihp vs P ihp). Cells plated on plastic expressed 5–23 fold less CAT. ECM stimulation also occurred in the absence of hydrocortisone: CAT expression was 33–45 fold reduced when the cells were plated onto plastic as compared to EHS (FIG. 6, E ip vs P ip). As observed previously, there was no CAT expressed in the absence of prolactin (FIG. 6). The regulation of the ER-1/BCE1 fusion by hormones and ECM reflected the expression pattern of the endogenous mouse β-casein gene and also the CAT expression pattern of bβcas–1790+42/CAT (Schmidhauser, et al., 1990) the disclosure of which is here by incorporated by reference. Thus the bβcas–121+42 promoter and the 160 bp enhancer BCE1 are sufficient to display the complete spectrum of regulation by hormones and ECM.

In order to further illustrate the invention, the following exemplary laboratory preparative work was carried out.

However, it will be appreciated that the invention is not limited to these examples or the details described therein.

EXAMPLE 1

To investigate whether or not BCE1 can exert an influence on a heterologous promoter, we placed BCE1 upstream of a viral promoters.

Figure 7:
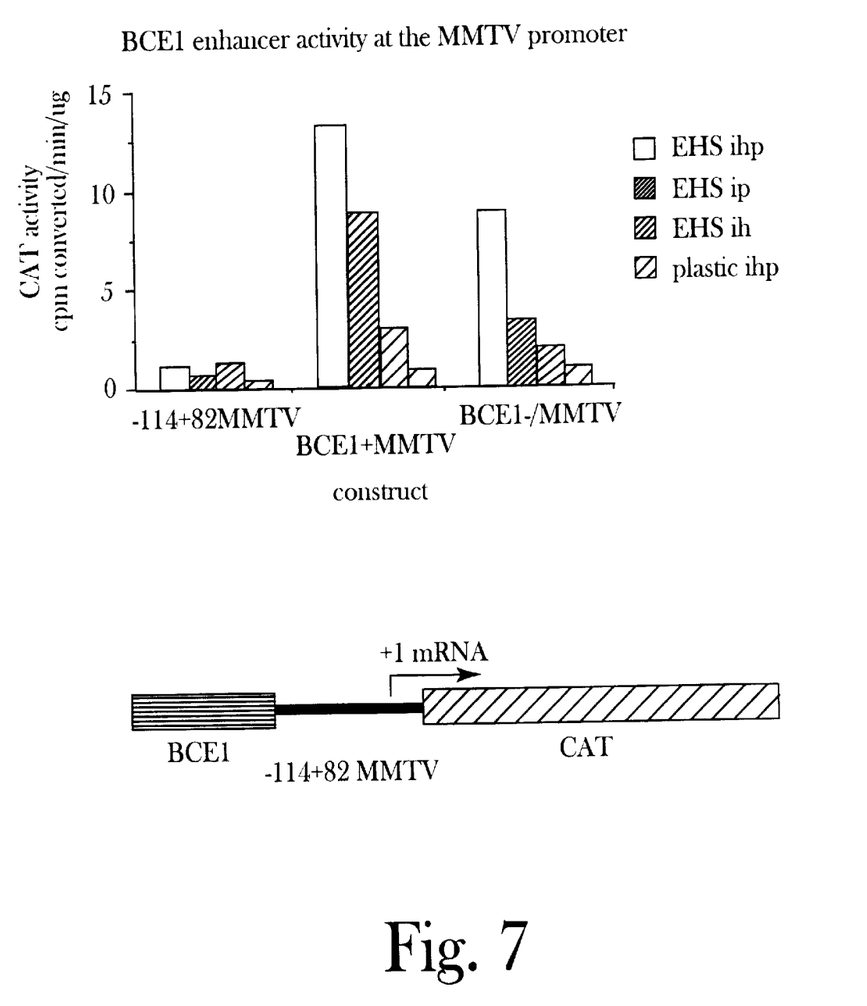
FIG. 7 Shows enhancer activity of BCE1 inserted at −114 of the MMTV long terminal repeat.

We then placed BCE1 upstream of a truncated form of the mouse mammary tumor virus long terminal repeat (MMTV LTR). This MMTV promoter extended from −114 to +82 (relative to the transcription start). While this segment of the MMTV promoter contains two glucocorticoid responsive elements (GRE), it has been reported to be non-responsive to glucocorticoids and to exhibit only basal transcriptional activity in L cells (Majors and Varmus, 1983). A comparison of the regulation of this promoter with and without BCE1 is shown in FIG. 7. CAT expression from the MMTV promoter alone was relatively weak (FIG. 7) but was regulated by hydrocortisone (1.9-fold stimulation) and by ECM (3.1-fold stimulation). The −114+82 MMTV promoter lacked any response to prolactin. The effect of BCE1 was striking (FIG. 7). BCE1 stimulated transcription from the MMTV promoter to very high levels (11.5-fold stimulation in the positive orientation, 7.9-fold increase when inverted, FIG. 7). Indeed, the BCE1/MMTV promoter fusions were 2 to 3-fold more active than the BCE1/ER-1 promoters (see FIG. 6).

BCE1 altered the pattern of regulation of the MMTV promoter as well as the level of activity. The BCE1/MMTV fusion promoter responded to prolactin (4.5-fold stimulation in cells cultured on EHS, FIG. 7) while the MMTV promoter alone did not. ECM-dependent induction of promoter activity was also greater for the BCE1-containing promoter. ECM stimulated CAT expression by the BCE1/MMTV fusion promoter 12 fold as compared with only 3 fold for MMTV alone (E ihp vs. P ihp, FIG. 7). Interestingly, the ECM and prolactin-dependent stimulation apparently mediated by BCE1 were mutually independent. Prolactin-stimulated CAT expression from the BCE1/MMTV fusion promoter 2.3-fold on plastic; ECM stimulated the same promoter 5.9-fold in the absence of prolactin).

EXAMPLE 2

Figure 8:
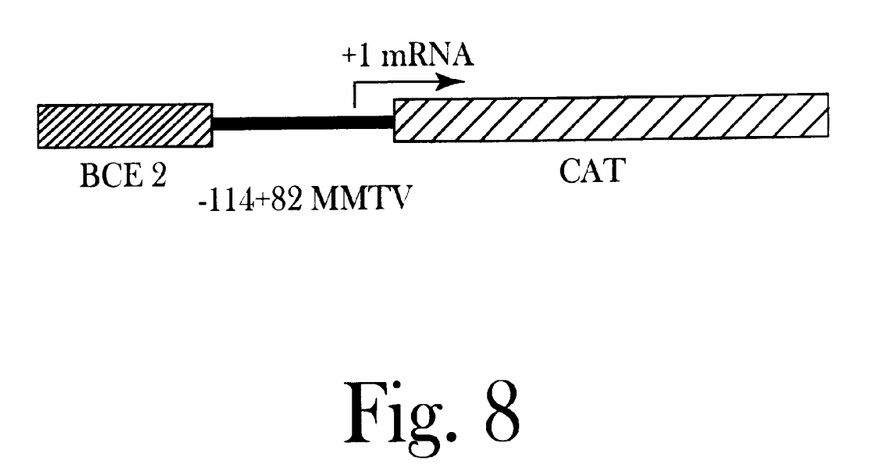
FIG. 8 Shows BCE2 fused to the MMTV promoter.

BCE2 is a DNA fragment similar in size to BCE1. Deletion of BCE2 resulted in greatly decreased transcriptional activity from the bβcas 5-flanking DNA (FIG. 3). It is envisioned that BCE2, if appropriately fused to a heterologous promoter, would exhibit enhancer activity similar to that of BCE1. BCE2 could be fused to the MMTV promoter and the CAT reporter gene (FIG. 8) in the same manner as disclosed herein for BCE1. This BCE2/MMTV/CAT construct could then be introduced into C1D9 cells and CAT activity assayed in the same manner as for BCE1.

Bovine β-casein gene and other major milk protein genes which include $\alpha_{s1}$-casein, $\alpha_{s2}$-casein, $\alpha$-casein, K-casein, Whey acidic protein, Alpha lactalbumin and Beta lactoglobulin should harbor useful enhancers other than BCE1 or BCE2 (whether they be related to BCE1 or BCE2 or not). These may be found by deletion mapping and functional analysis as described herein for BCE1. The 5'-flanking region from the major milk protein gene, including the promoter, would be fused to CAT at a site downstream of the transcription initiation site (see FIG. 2 for the comparable bβcas construct). This construct would be introduced into C1D9 cells and CAT activity determined. Progressive deletions from the 5' end of said major milk protein DNA (as shown in FIG. 2 for bβcas) and subsequent assay in C1D9 cells would identify active enhancer regions as for bβcas (see FIG. 3). Similarly, regions of bβcas or other major milk protein genes, other than the 5'-flanking DNA (such as the structural genes or 3'-flanking DNA) may be introduced into constructs such as in FIG. 2 for deletion mapping and functional analysis. Further, deletions need not be made solely from the 5' end or in the 3' direction of such major milk protein DNA (as it is in FIG. 2) but may be made in either direction from internal sites or from either end (so long as such deletions do not encompass the promoter). DNA sequences identified by such deletion mapping and functional analysis may then be tested for enhancer activity by fusion to promoters such as −121+42bβcas (see FIG. 6) or −114+84MMTV (see FIG. 7). These constructs would be introduced into C1D9 cells and CAT activity determined as for BCE1.

Those skilled in this art will appreciate that minor substitutions can be made to the novel enhancers without adversely or detrimentally affecting their biological activity as defined herein and are intended to be within the scope of this invention. It is envisioned that each nucleotide in the primary sequence disclosed herein for BCE1 and BCE2 will not prove to be essential for enhancer activity. Individual binding sites for transcription-modulating nuclear proteins tend to be small, present in multiple copies and separated by sequences that are dispensable or necessary only to preserve appropriate spacing between the active elements of the enhancer (see Serfling et al, 1985; Muller and Schaffner, 1988; Kriegler, 1990). Thus, changes in the nucleotide sequence of BCE1 (or BCE2) that do not disrupt binding of nuclear proteins nor alter the spacing between binding sites may have no effect on enhancer activity. Were the precise binding sites for nuclear proteins within BCE1 or BCE2 (eg.) known, it would be within the state of the art to substantially alter the nucleotide sequence of BCE1 or BCE2 without compromising its enhancer activity. Conversely, it would also be within the state of the art to substantially alter or destroy the enhancer activity with relative minor changes in the nucleotide sequence of BCE1.

From the foregoing description, one skilled in the art can easily ascertain the essential characteristics of this invention, and without departing from the spirit and scope thereof, can make various changes and modifications of the invention to adapt it to various usages and conditions. Accordingly the scope of the invention is not to be considered limited to the particular embodiments shown of suggested, but is rather to be determined by reference to the appended claims.

REFERENCES

Zurflub, L. L., Bolten, S. L., Byatt, J. C., McGarth, M. F., Tou, J. S., Zupee, M. E., Krivi, G. G. (1990) *Growth Factors* 3, 257–266.

Gorodetsky, S., Tkach, T. M., Kapelinchaya, T. V. (1990) *Gene* 66, 87–96.

Mahinlay—Sequence of βcasein gene.

Danielson, K. G., Oborn, C. J., Durban, E. M., Buetel, J. S., Medina, D. (1984) *Proc. Natl. Acad. Sci. USA* 81, 3756–3760.

Barcellos-Haff, M. H., Aggler, J., Ram, T. G., Bissell, M. J. (1989) *Development* 105, 223–235.

Neuman, J. R., Morency, C. A., Russian, K. O. (1987) *Bio Technology* 5, 444–447.

Gorman, C. (1986) in *DNA Cloning: High Efficiency Gene Transfer into Mammalian Cells,* ed. Glover, D. M. (IRL, Oxford), pp. 143–211.

Chomczynski, P., Sacchi, N. (1987) *Anal. Biochem* 162, 156–159.

Feinberg, A. P., Vogelstein, B. V. (1984) *Anal. Biochem.* 137, 266–267.

Schmidhauser, C., Bissell, M. J., Myers, C. A., Casperson, G. F. (1990) *Proc. Natl. Acad. Sci. USA* 87, 9118, 9122.

Sambook, J., Fritach, E. F. and Maniatis, T. (1989) Molecular Cloning, a laboratory manual. (Cold Spring Harbor: Cold Spring Harbor Laboratory Press).

Majors, J., Varmus, H. E. (1983) *Proc. Natl. Acad. Sci. USA* 80, 5866–5870.

Richards, D. A., J. R. Rogers, S. C. Supowit and J. M. Rasen (1981) *J. Biol. Chem.* 256, 526.

Willis, I. M., A. F. Stewart, A. Caputo, A. R. Thompson and A. G. MacKinlay (1982) *DNA* 1, 375.

Yu-Lee, L-Y and J. M. Rosen (1983) *J. Biol. Chem.* 258, 10794.

Campbell, S. M., J. M. Rosen, L. G. Hennighausen, U. Strech-Jurk and A. E. Sippel (1984) *Nucleic Acids Res.* 12, 8685.

Jones, W. K., L-Y Yu-Lee, S. M. Clift, T. L. Brown and J. M. Rosen (1985) *J. Biol. Chem.* 260, 7042.

Yu-lee, L-Y, L. Richter, C. H. Couch, A. F. Stewart, A. G. Mackinlay and Jim Rosen (1986) *Nucleic Acids Res.* 14, 1983.

Rosen, J. M. (1987) In: The Mammary Gland: Development, Regulation and Function (M. C. Neville and C. Daniel, Eds.) Plenum Publishing, New York: pp. 301.

Maniatea, T., S. Goodbourne, J. A. Fischer (1987) *Science* 236, 1238.

Serfling, E., M. Jansin, W. Schaffner (1988) *Trends Genet* 1, 224.

Grosschedl, R., M. L. Bernsteil (1980) *PNAS* 77, 1432.

Banerji J., S. Rusroni, W. Schaffner (1981) *Cell* 27, 299.

Gillies, S. D., et al., (1983) *Cell* 33, 717.

Baneryi J., L. Olsen, W. Schaffner (1983) *Cell* 33, 729.

Kaufman, R. J. (1990) *Meth Eng.* 185, 487.

Johnston, M. (1987) *Microbial Reviews* 51, 458.

Kriegler, M. (1990) *Meth. Eng.* 185, 512. (Not in text yet.)

Hearing P., T. Schenk (1986) *Cell* 45, 229.

Campbell, MEM, J. W. Palfreyman, C. M. Preston (1984) *JMB* 180, 1–20.

Chomczynski, P. and N. Sacchi (1987) *Anal. Biochem.* 162, 156.

Feinberg, A. P. and B. V. Vogelstein (1984) *Anal. Biochem.* 137, 266.

Sanger, F., A. R. Coulson, G. F. Hong, D. F. Hill and G. B. Peterson (1977) *J. Mol. Biol.* 162, 729.

Mercier, J-C., P. Gage, S. Soulier, D. Hue-Delahaie and J-L Vilotte (1985) *Biochimie.* 67, 959.

Lee, K-F, F. J. DeMago, S. H. Atiee, J. M. Rosent (1988) *Nucleic Acids Res.* 16, 1027.

Bayna, T. A. and J. M. Rosen (1990) *Nucl. Acids Res.* 18, 2977.

Burdon, T., L. Sanharan, R. J. Wall, M. Spencer and L. Hennighausen (1991) *J. Biol. Chem.* (WAP in Tm's)

Simons, J. P., M. McClenaghan and A. J. Clark (1987) *Nature* 328, 530.

Manchio, A., P. M. Brichell, D. Kroussis, A. L. Mellar, D. Katy and R. K. Craig (1991) *Biochem. J.* (gp-d lac in Tm's).

Vilotte, J-L, S. Soulier, M-G Stinnabre, M. Massoud and J-C Mercier (1989) *Eur. J. Biochem.* 186, 43.

Lee, K-F, S. H. Atiee and J. M. Rosen (1989) *Mol Cell. Biol.* 9, 560.

Schnenberger, C-A, A-C Andres, B. Groner, M. van der Valk, M. LeMeur and P. Gerlinger (1988) *EMBO J.* 7, 169.

Andres, A-C, C-A Schnenberger, B. Groner, L. Hennighausen, M. LeMeur and P. Gerlinger (1987) *Prac. Natl. Acad. Sci., USA* 84, 1299.

Pittius, C. W., L. Hennighausen, H. Westphal, E. Nichols, J. Vitale and K. Gordon (1988) *Proc. Natl. Acad. Sci.. USA* 85, 5874.

Gordon, K., E. Lee, J. A. Vitale, A. E. Smith, H. Westphal and L. Hennighausen (1987) *Biotechnol* 5, 1183.

Ebert, K. M., J. P. Selgrath, P. DiTullo, J. Denman, T. E. Smith, M. A. Memon, J. E. Schindler, G. M. Monastershy, J. A. Vitale and K. Gordon (1991) *Biotechnol.* 2, 835.

Lee, K-F, S. H. Atiee and J. M. Rosen (1989) *Molec. Cell Biol.* 9, 560.

Lee, K-F, Shatiee, H. Henning and J. M. Rosen (1989) *Molec. Endocrinol.* 3, 447.

Buhler, T. A., T. Buyère, D. F. Went, G. Stranzinger and K. Bürhi (1990) *Biotechnol.* 8, 140.

Clark, A. J., H. Bessos, J. O. Bishop, P. Brown, S. Harris, R. Lathe, M. McClenaghan, C. Prowse, J. P. Simons, C. B. A. Whitelaw and I. Wilmut (1989) *Biotechnol.* 7, 487.

Simons, J. P., I. Wilmut, A. J. Clark, A. L. Archibald, J. O. Bishop and R. Lathe (1988) *Biotechnol.* 6, 179.

Wright, G., A. Carver, D. Cotton, D. Reeves, A. Scott, P. Simons, I. Wilmut, I. Garner and A. Colman (1991) *Biotechnol.* 9, 830.

Meade, H., L. Gates, E. Lacy and N. Lonberg (1990) *Biotechnol.* 8, 443.

Ball, R. K., R. R. Früs, C-A Schonenberger, W. Doppler and B. Groner (1988) *EMBO J.* 7, 2089.

Doppler, W., A. Villunger, P. Jennewein, K. Brduscha, B. Groner and R. K. Ball (1991) *Molec. Endocrinol.* 5, 1624.

Doppler, W., B. Groner and R. K. Ball (1989) *Proc. Natl. Acad. Sci. USA* 86, 104.

Yashimura, M. and T. Oha (1990) *Proc. Natl. Acad. Sci. USA* 87, 3670.

Ivanov, V. N., A. A. Kabilev, S. I. Gorodetshü and V. A. Gribanovskü (1990) *Molel. Biol. USSR*) 24, 1605.

Grabishev, A. A., E. M. Klenova, V. A. Gribanovskü and S. I. Gorodetshü (1990) *Doklady Akademü Nauk SSSR* 315, 997.

Lubon, H. and L. Hennighausen (1987) *Nucleic Acids Res.* 15, 2103.

Lubon, H. and L. Hennighausen (1988) *Biochem. J.* 256, 391.

Lee, C. S. and T. Oka (1992) *J. Bio. Chem.* 267, 5797.

Schmitt-Ney, M., W. Doppler, R. K. Ball and B. Groner (1991) *Molec. Cell Biol.* 11, 3745.

Schmitt-Ney, M., B. Happ, R. K. Ball and B. Groner (1992) *Proc. Natl. Acad. Sci. USA* 89, 3130.

---

What is claimed is:

1. An isolated DNA, which comprises the sequence shown in FIG. 4 (SEQ ID NO:1) and wherein said DNA is not more than 500 nucleotides in length.

2. The DNA as recited in claim 1 wherein said DNA consists of the sequence as shown in FIG. 4 (SEQ ID NO:1).

3. An isolated DNA, which comprises the sequence shown in FIG. 5 (SEQ ID NO:2) and wherein said DNA is not more than 500 nucleotides in length.

4. The DNA as recited in claim 3 wherein said DNA consists of the sequence as shown in FIG. 5 (SEQ ID NO:2).

5. An expression vector, comprising:
 a) an enhancer comprising the sequence shown in FIG. 4 or 5 (SEQ ID NOS:1 or 2);
 b) a heterologous eukaryotic promoter operably linked to said enhancer which includes a proximal transcriptional control element and a transcription start site;
 c) a DNA encoding a protein wherein said DNA is operably linked downstream of said promoter; and
 d) a terminator operably linked downstream of said DNA encoding a protein which terminator includes a transcriptional termination signal and a polyadenylation site.

6. The expression vector as recited in claim 5 wherein said heterologous eukaryotic promoter is a mouse mammary tumor virus promoter.

7. The expression vector as recited in claim 5 wherein said promoter is a promoter from a gene which encodes a protein other than a major milk protein gene.

8. The expression vector as recited in claim 5 wherein said enhancer is not more than 500 nucleotides in length.

9. The expression vector as recited in claim 5 wherein said enhancer consists of the sequence as shown in FIG. 4 or FIG. 5 (SEQ ID NOS:1 or 2).

10. A cell transformed by the expression vector as recited in claim 5.

* * * * *